United States Patent
Lorentz

(10) Patent No.: US 10,041,232 B2
(45) Date of Patent: Aug. 7, 2018

(54) SELF-MAINTAINING AUTOMATIC FLUSHING VALVE WITH INTERNAL FREEZE PROTECTION

(71) Applicant: John C. Kupferle Foundry Company, St. Louis, MO (US)

(72) Inventor: Daniel C. Lorentz, St. Louis, MO (US)

(73) Assignee: John C. Kupferle Foundry Company, St. Louis, MO (US)

( * ) Notice: Subject to any disclaimer, the term of this patent is extended or adjusted under 35 U.S.C. 154(b) by 24 days.

(21) Appl. No.: 15/306,711

(22) PCT Filed: May 27, 2015

(86) PCT No.: PCT/US2015/032685
§ 371 (c)(1),
(2) Date: Oct. 25, 2016

(87) PCT Pub. No.: WO2015/183962
PCT Pub. Date: Dec. 3, 2015

(65) Prior Publication Data
US 2017/0051478 A1 Feb. 23, 2017

Related U.S. Application Data

(60) Provisional application No. 62/003,391, filed on May 27, 2014.

(51) Int. Cl.
*E03B 7/12* (2006.01)
*E03B 7/07* (2006.01)
*F16K 31/06* (2006.01)
*F16K 37/00* (2006.01)
(Continued)

(52) U.S. Cl.
CPC ............... *E03B 7/12* (2013.01); *E03B 7/071* (2013.01); *F16K 31/0675* (2013.01);
(Continued)

(58) Field of Classification Search
CPC ... E03B 7/10; E03B 7/12; E03B 7/071; F16K 49/002; F16K 37/0083; F16K 37/0091;
(Continued)

(56) References Cited

U.S. PATENT DOCUMENTS 5,427,350 A * 6/1995 Rinkewich ............. A01G 25/16
137/625.22
5,470,043 A 11/1995 Marts et al.
(Continued)

FOREIGN PATENT DOCUMENTS

JP 2005213809 A 8/2005
KR 2020090010810 U 10/2009

OTHER PUBLICATIONS

International Search Report for PCT application PCT/US2015/032685 dated Aug. 24, 2015.
(Continued)

*Primary Examiner* — Ian Paquette
(74) *Attorney, Agent, or Firm* — Sandberg Phoenix & Von Gontard P.C.

(57) ABSTRACT

A water flushing and sampling device (1) comprising a valve (33) operable to flush water from a subterranean source through the device. A turbine (73) downstream of an outlet nozzle (37) is operable to generate electricity when water is flushed through the device. An enclosure (13) contains the valve, a temperature sensor (81) operable to sense temperature within the enclosure, a heater (77, 83) operably connected to the turbine and being operable to heat the enclosure, and a control system (91) operable to open the valve to cause the turbine to operate the heater when the temperature sensor indicates the approach of a dangerously low temperature.

20 Claims, 10 Drawing Sheets

(51) Int. Cl.
*F16K 49/00* (2006.01)
*G01N 33/18* (2006.01)

(52) U.S. Cl.
CPC ...... *F16K 37/0083* (2013.01); *F16K 37/0091* (2013.01); *F16K 49/002* (2013.01); *G01N 33/18* (2013.01)

(58) Field of Classification Search
CPC ...... F16K 31/0675; F16K 21/00; F16K 21/04; F16K 21/16; F16K 49/00; F16K 27/12; G01N 33/18
USPC .......... 137/334; 236/1 C; 237/2 R, 2 A, 8 R, 237/8 A, 56
See application file for complete search history.

(56) References Cited

U.S. PATENT DOCUMENTS

| | | | |
|---|---|---|---|
| 5,496,733 A * | 3/1996 | Spandau | G01N 1/34 |
| | | | 436/52 |
| 5,614,119 A | 3/1997 | Ollis | |
| 5,921,270 A | 7/1999 | McCarty | |
| 6,021,664 A | 2/2000 | Granato et al. | |
| 6,035,704 A | 3/2000 | Newman | |
| 6,635,172 B2 | 10/2003 | Newman | |
| 6,837,271 B1 * | 1/2005 | Saint | G01M 3/2807 |
| | | | 137/460 |
| 7,093,608 B2 | 8/2006 | Taylor | |
| 7,178,739 B2 | 2/2007 | Taylor | |
| 8,733,390 B2 | 5/2014 | McKeague | |
| 2003/0168518 A1 | 9/2003 | Beida et al. | |
| 2012/0298208 A1 | 11/2012 | Taylor et al. | |
| 2014/0174556 A1 * | 6/2014 | Herbert | E03C 1/057 |
| | | | 137/78.1 |

OTHER PUBLICATIONS

Written Opinion of the International Search Authority for PCT application PCT/US2015/032685 dated Aug. 24, 2015.

* cited by examiner

SELF-MAINTAINING AUTOMATIC FLUSHING VALVE WITH INTERNAL FREEZE PROTECTION

CROSS-REFERENCE TO RELATED APPLICATIONS

This application is a national stage application under 35 U.S.C. § 371 of International application No. PCT/US2015/032685, filed 27 May 2015, which is related to, and claims the benefit of U.S. Provisional Application Ser. No. 62/003,391, filed 27 May 2014, the contents of which are hereby incorporated by reference.

STATEMENT REGARDING FEDERALLY SPONSORED RESEARCH

Not applicable.

BACKGROUND OF THE INVENTION

Automatic flushing valves are now widely used for flushing and testing water in dead ends of water systems. Examples of such systems are shown in McCarty, U.S. Pat. No. 5,921,270, Newman, U.S. Pat. Nos. 6,035,704 and 6,635,172, Taylor, U.S. Pat. Nos. 7,093,608 and 7,178,739, Taylor et al., U.S. published application US 2012/0298208 A1, and McKeague, U.S. Pat. No. 8,733,390. Somewhat similar systems have been used for monitoring and flushing ground water sources, as shown for example in Granato et al, U.S. Pat. No. 6,021,664. All of the patents and patent publications mentioned herein are hereby incorporated by reference.

Automatic flushing valves can be controlled by simple timers, or they can be controlled by complex computers such as programmable logic controllers (PLCs), which may in turn be internally programmed or may be controlled through a supervisory control and data acquisition (SCADA) interface. Such systems may periodically test for the concentration of chlorine (usually in the form of a hypochlorite salt), or for contaminants such as minerals, like lead or iron, or microbiological hazards, or for other characteristics of the water supply to which they are attached, and then activate flushing, alarms, water treatment, or other responses if these measures are out of specification.

Because automatic flushing valves are frequently located at a distance from an electrical power source, they are generally powered by batteries, and the batteries are recharged, if necessary, by a renewable source such as solar cells or a turbine run by the water being flushed.

Automatic flushing valves are frequently located in places subject to freezing temperatures. Because freezing water can damage the valve and its associated piping and controls, and because freezing temperatures may interfere with operation of the electronics associated with the valve, the valves in such situations are buried below the frost line or are placed in heavily insulated enclosures. Even such precautions, however, are not always sufficient to prevent damaging chilling of the valve and its associated controls and electronics. For example, in Granato et al, U.S. Pat. No. 6,021,664, Working Example Two, the system was twice shut down by freezing.

BRIEF SUMMARY OF THE INVENTION

In accordance with the present invention a device connected to a subterranean water supply is provided that senses the temperature inside an enclosure for the unit and provides heat through energy generated by a turbine generator when the temperature approaches a critical level. An electrical resistive dissipater, electrically connected to the turbine generator to prevent overcharging storage batteries within the enclosure, may act as a heater, or a separate high efficiency heater (such as a fan-heater) may be provided, or both. The device is illustratively a water flushing device or a water sampling device; in an embodiment, it is both. Additional heat may be provided to critical components, such as sampling lines, by providing electrical resistance heated tracers.

The enclosure is preferably insulated to a thermal resistance of at least about R-5 (U.S.) (R-0.9 SI), and in preferred embodiments the thermal resistance of the enclosure is at least about R-9 (U.S.) (R-1.6 SI).

In accordance with a presently preferred embodiment of the invention, the turbine is located downstream of an outlet of the flushing device, so that it provides no impediment to flow through the device. A nozzle is preferably provided in the outlet to control the rate at which water is expelled in accordance with the head pressure of the underground water system and the capacity of the turbine. The nozzle may also guide the exit stream into vanes of the turbine.

The system may be programmed to expel water on a timed basis or may periodically or continuously expel a small sample of water for automated testing, then make a cleansing draw (flush) to expel water when the sample is out of specifications. For example, a small sample stream may be drawn across or through a chlorine sensor, and a set amount of water flushed when the chlorine level drops below a predetermined value; a new sample may then be tested if desired.

Alternatively, the chlorine level may be sampled continuously during flushing, with flushing stopping when the chlorine level reaches a predetermined value.

The turbine preferably operates to charge the batteries whenever water is flushed through the system. After the batteries have reached their desired charge condition, excess power generated by the turbine is dumped to one or more dissipaters in the form of large electrical resistors, thereby providing a trickle charge to the batteries while preventing overcharging. Such systems are commonly known as diversion controlled charging systems, having bulk and float charging stages. The dissipaters also tend to warm the enclosure and reduce the incidence of excessively low temperatures within the enclosure.

The system may also begin flushing whenever a high energy use activity begins, such as broadcasting data over a high-powered radio, in order to generate power and avoid draining the batteries.

When the system senses that the batteries are in need of charging, as by sensing a drop in voltage below a predetermined value, an override routine causes flushing to be initiated and continued until a set period after the batteries are charged, during which period the dissipaters prevent overcharging while providing a trickle charge to the batteries.

Likewise, when a temperature sensor within the enclosure senses that the temperature has dropped below a critical value, such as a value in the range of 35-39° F. (1 to 4° C.), an override routine causes flushing to be initiated to allow activation of a heater to raise the temperature of the enclosure to a predetermined value, such as a value in the range of 42-50° F. (5 to 10° C.). Any style of temperature sensor or thermostat may be utilized. Illustratively, a thermostat, thermocouple, or resistance temperature detector (RTD) is placed on each of the four corners of the enclosure, positioned to sense the coldest temperatures within the enclosure. Illustratively, they are placed at about the height of a water passage within the enclosure.

The device may optionally include a vent in the enclosure and may also optionally include a fan for cooling the enclosure when temperatures within the enclosure become excessive. For example, insulated temperature-controlled louvers may be provided, and the fan portion of a fan-heater may be run to provide cooling. The enclosure may also be cooled by flushing water while the turbine is electrically disconnected.

The device of the invention is preferably self-contained, self-maintaining, and surface-mounted. These characteristics make the device far easier to ship, install, and maintain than previously known devices. Because the device is preferably not buried but rather installed on top of the ground, installing it and accessing it are easier. Because it reliably prevents freezing, its piping system, controls, and electronics are more robust than those of previous such devices. The device may transmit information relating to water conditions, such as chlorine levels, contaminant levels, pH, turbidity, conductivity, oxidation reduction potential (ORP), trihalomethane (THM), pressure, and water temperature, as well as information relating to its own status, such as inside and outside temperature, flushing times and duration, flow rate, valve status, totalized flow, battery charge, battery discharge and charging rates, and any malfunctions or out-of-specification readings.

In an embodiment, two outlets are provided in the system, one running the turbine and the other discharging without running the turbine. This arrangement allows for high discharge rates while controlling the speed and power output of the turbine so as not to overdrive it. For example, the turbine may limit flow to fifty gallons per minute, while complete flushing in a reasonable time may require a flow rate of one hundred fifty gallons per minute. If the two outlets are individually controlled, the duty cycle of the turbine generator may be shortened, dumping of excessive amounts of water during battery-charging and heating cycles may be avoided, and the temperature of the enclosure lowered during hot weather by not running the turbine.

Other aspects of the invention will be recognized by those skilled in the art in light of the following description, drawings, and claims.

DESCRIPTION OF THE PREFERRED EMBODIMENT

Figure 1:
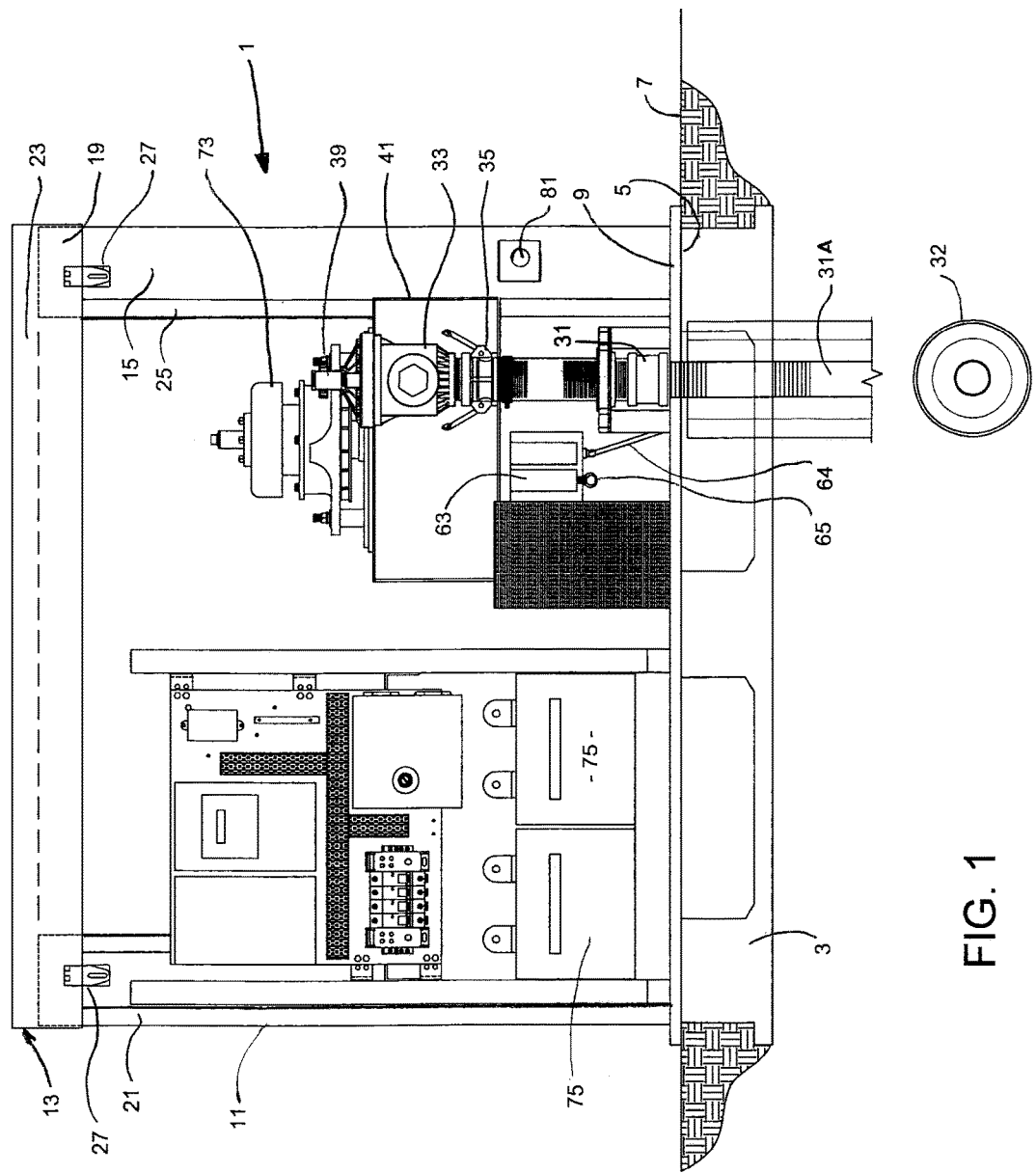
FIG. 1 is a view in front elevation of a water flushing and sampling device in accordance with an embodiment of the present invention, the device being mounted on a base connected to a subterranean water source and a subterranean drain, a front enclosure cover and two front support posts being removed.
Figure 2:
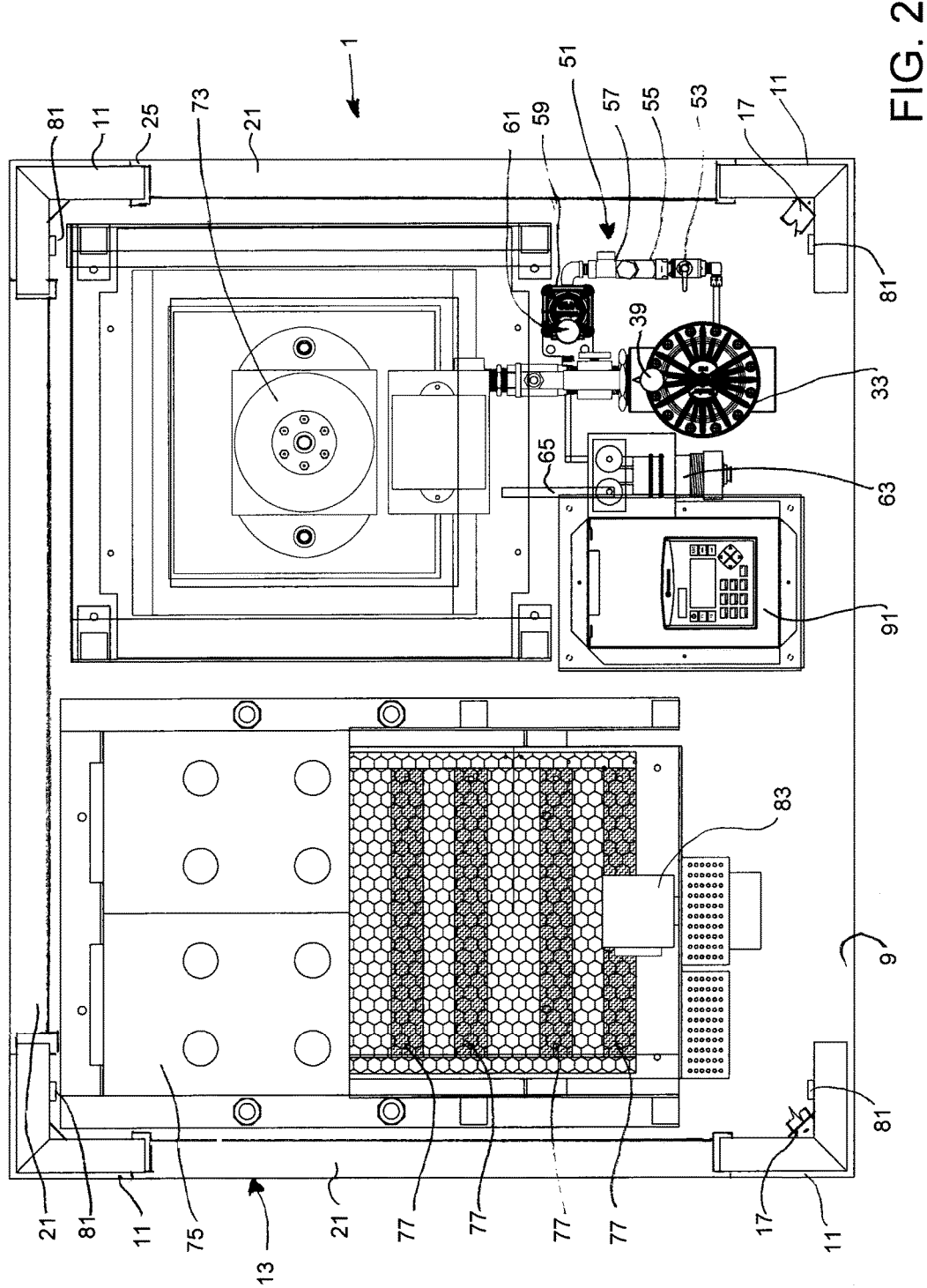
FIG. 2 is a top plan view thereof, with a top enclosure cover, a top frame, and a front enclosure cover removed.
Figure 3:
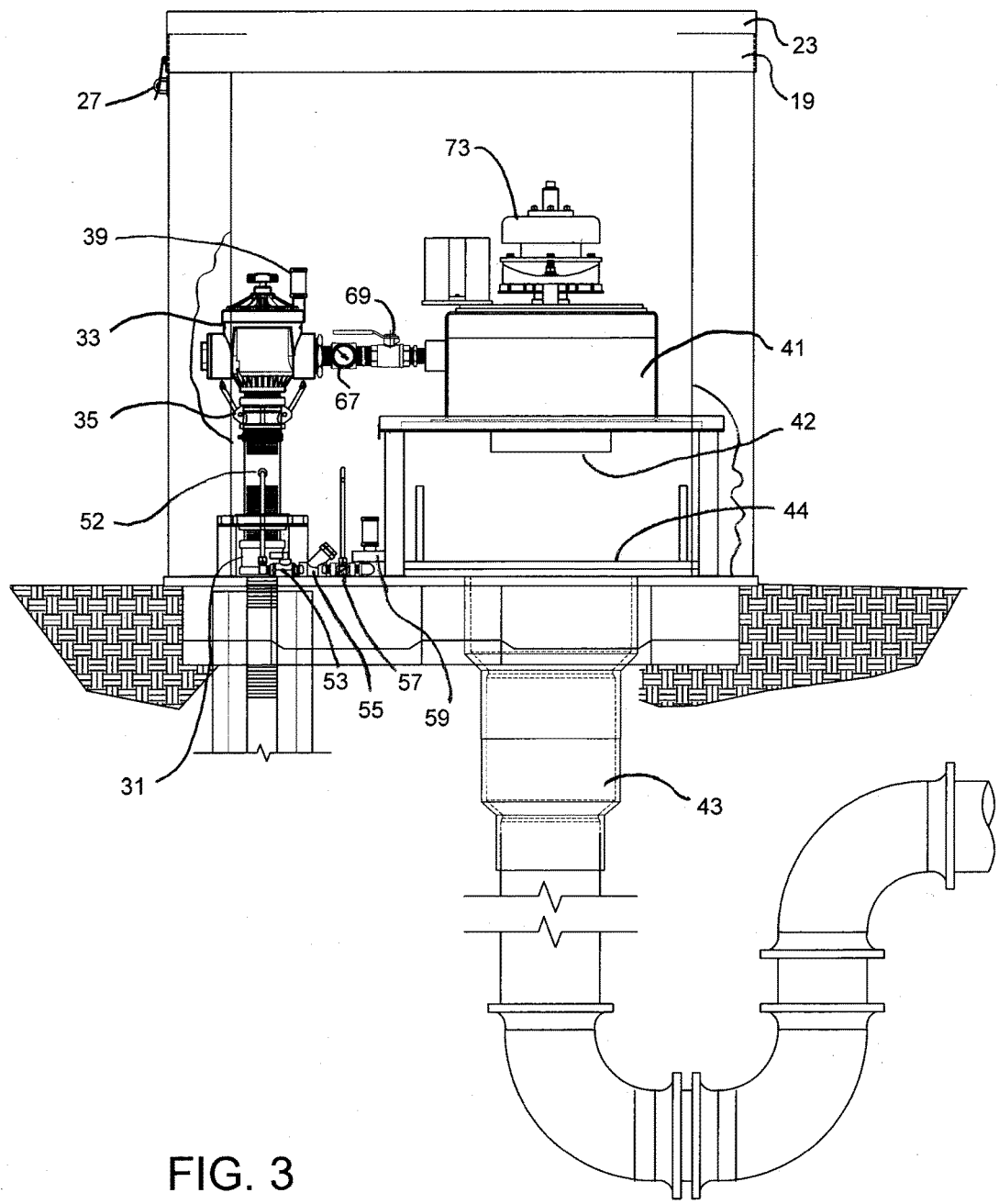
FIG. 3 is a view in right side elevation of the device of FIGS. 1 and 2, with a right side insulation panel removed.

Referring now to the drawings, one illustrative embodiment of a device 1 in accordance with the invention is shown. The device in this illustrative embodiment is a flushing and sensing unit designed to monitor water quality and flush water when a water characteristic (e.g., chlorine concentration) falls outside a predetermined parameter (e.g., too low a concentration). Other flushing criteria may also be utilized, such as turbidity, or the device may flush on a regular timed schedule or on command of a remote operator.

The device 1, in this illustrative embodiment, is mounted on a plastic base 3. The base 3 may act as a pallet during shipping. The base 3 is set into the ground, so that its top surface 5 is generally flush with the ground surface 7.

The device 1 includes a floor 9 having four upright corner posts 11, which support an enclosure 13. The posts 11 include strips 15 of expanded closed cell polyisocyanurate insulation on their inner faces. Cross braces 17 at the upper ends of the posts 11 stabilize the posts 11. The enclosure 13 includes four side slabs 21 which fit between the corner posts 11, and a cover slab 23 which fits over the posts 11. The side slabs 21 and cover slab 23 are formed of 1.5" (4 cm) sheets of expanded closed cell polyisocyanurate insulation having an inner fiberglass skin. The insulation is adhered to an outer powder-coated aluminum facing sheet. The facing sheets adhered to the side slabs 21 are bent in at their upper and lower margins to protect the ends of the foam slabs. At their sides, the facing sheets are bent to form U-shaped channels 25 at the ends of the slabs 21. The channels 25 allow the slabs 21 to slide over the posts 11 from the top. The aluminum facing sheet on the cover slab 23 is bent down at its edges to form flaps 19. The insulated enclosure illustratively has an R-9 U.S. (R-1.6 SI) thermal resistance, although the amount of insulation is generally determined by the climate of the location of the device and by how cold the environment is expected to be. The enclosure can be locked with hasps 27.

The enclosure 13 is assembled by sliding the channels 25 of the side slabs 21 over the posts 11 from the top, then placing the cover slab 23 over them and the posts, locking the enclosure with pins (not shown) on the rear lip 19 and hasps 27 on the front lip 19.

A 2" FIP inlet pipe 31 attaches to an in-ground inlet pipe 31A which leads vertically from a subterranean source of pressurized water 32 to the bottom of a 2" automatic flushing valve 33 held to the inlet pipe 31 by a stainless steel quick-disconnect coupling 35. The source of pressurized water is illustratively a piped municipal water system.

The flushing valve 33 controls the flow of pressurized water through the device between the inlet pipe 31 and an outlet nozzle 37. The flushing valve closes and opens using the extension and retraction of an electric DC latching solenoid 39. As is known in the art, latching solenoids are bistable and require only a pulse to change their state. An example of such a solenoid, as well as its control circuit, is described in Marts, et al., U.S. Pat. No. 5,470,043.

In the illustrative embodiment, the nozzle 37 discharges into a turbine splash chamber 41. The chamber 41 is provided with a lower exit 42 onto a splash pad 44, so as to produce an air gap between the chamber 41 and a sewer 43 or other underground receptacle; it otherwise drains by overflowing onto the ground around the device 1. If desired or required, overflowing water may be treated to remove chlorine.

Just downstream of the inlet, upstream of the flushing valve 33, a chlorine sensing system 51 is tapped into the inlet pipe 31 as indicated at 52. The chlorine sensing system 51 includes a manual shutoff 53, a filter 55, a sample access port 57, a solenoid sampling valve 59 including a solenoid 61 for controlling flow through the system 51, and a membrane chlorine sensor 63, having an inlet 64 and an outlet 65. The shutoff valve 53, filter 55, and sample access port 57 prevent debris from entering the flow cell as well as allowing for maintenance. The chlorine sensor is amperometric, using a membrane sensor which measures chlorine directly without the use of reagents. Water simply flows past the sensor and directly to the drain 65, with the flow rate and pressure across the sensor controlled by the constant head flow cell assembly 63.

The main automatic, solenoid-controlled blow-off valve 33 permits flow from the inlet 31, through a pressure gauge 67, a manual shutoff 69, and outlet nozzle 37. Water exiting the outlet 37 is directed at and drives the vanes or baskets of Pelton wheel 71 of an electric turbine generator 73. The turbine generator 73 is illustratively a 450-watt generator, producing 30-33 volts DC at twenty amps when driven by a flow of fifty gallons per minute. Changes in flow rate will affect the rate of power generation, but will not have a major effect on the operation of the device 1.

Figure 4:
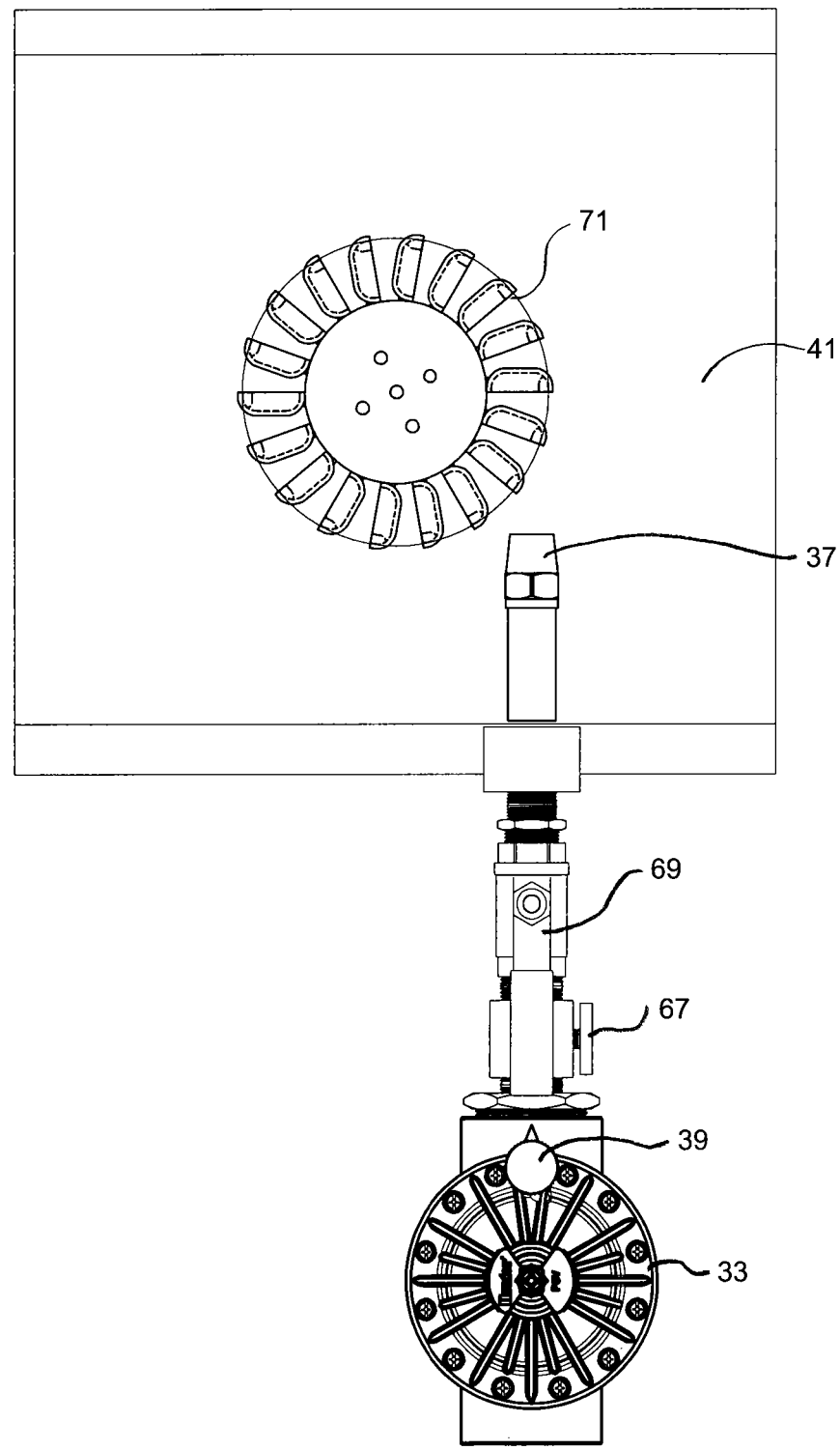
FIG. 4 is a detail in top plan, with a lid and generator structure removed, showing a discharge nozzle and a Pelton wheel part of a turbine generator portion of the device of FIGS. 1-3.
Figure 5:
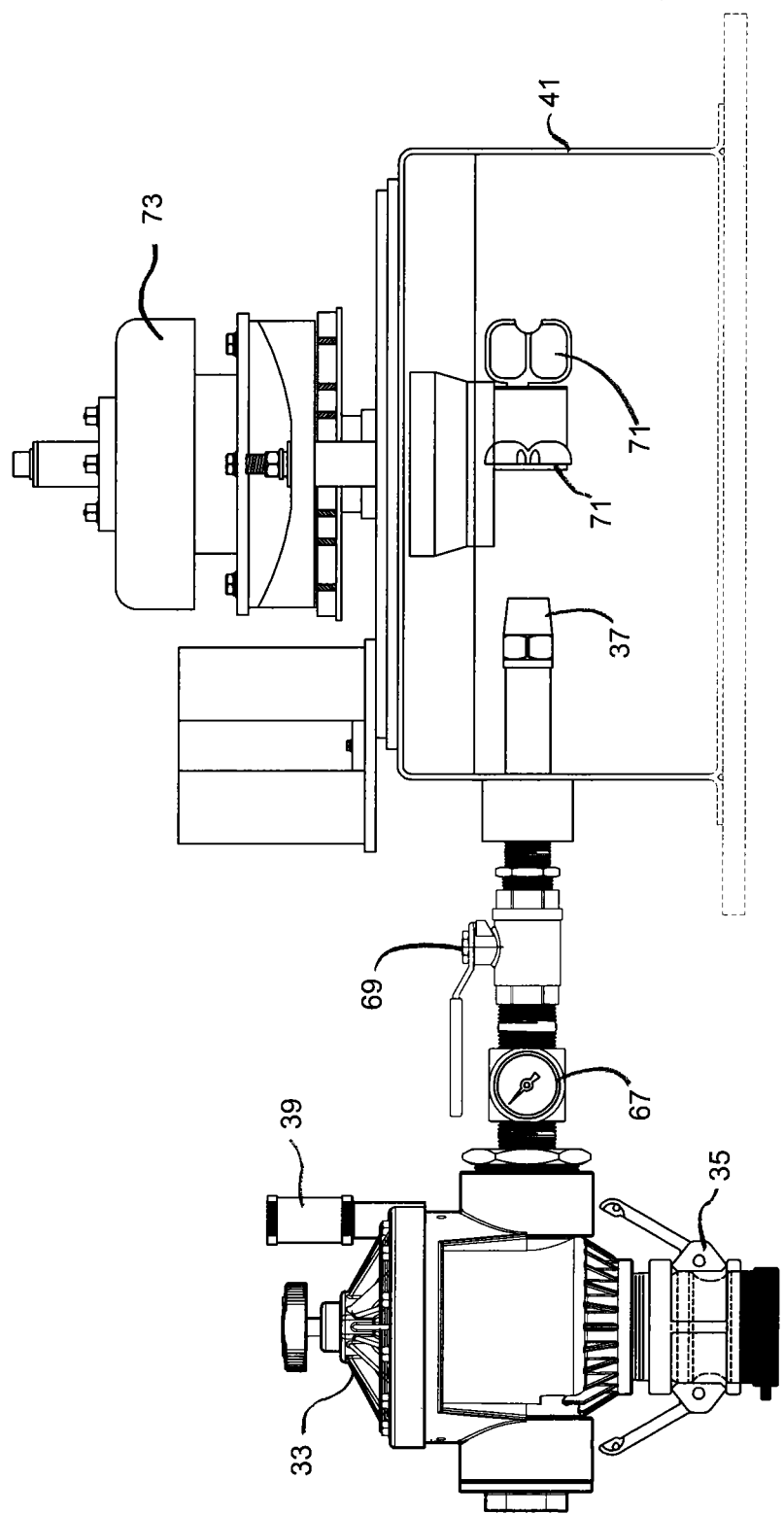
FIG. 5 is a detail in right side elevation, partially cut away, showing the discharge nozzle and Pelton buckets.

As shown in FIGS. 4 and 5, release of the quick-disconnect coupling 35 allows the valve 33, the nozzle 37, the turbine 73, and the chamber 41 to be lifted from above as a unit, enabling easy servicing of these major components.

The generator 73 charges 210 amp hour deep charge batteries 75 until they are fully charged, then dumps power to dissipaters (electric resistors) 77, under the control of redundant diversion controllers 79 which sense the voltage and switch some of the flow of power from the generator 73 to the dissipaters 77. The diversion controllers 79 may include digital or analog voltage displays, and the inputs those displays may be utilized to send information about the frequency and duration of battery charging cycles to a remote operator. Because battery voltages fluctuate with temperature changes, the diversion controllers 79 receive battery temperature information and compensate automatically for temperature changes.

Temperature sensors 81 are mounted to the insulation strips 15 on the enclosure corner posts 11, at about the height of the main valve 33. The temperature sensors are illustratively snap-acting bimetal disc type thermostats, constructed to operate at a fixed pre-selected temperature. As described hereinafter and in the drawings, the temperature sensors 81 control activation of a high-efficiency fan heater 83. The fan heater 83 is illustratively a STEGO model 04640.1-00.

All activities of the illustrative flushing and monitoring device 1 are controlled by a programmable logic controller (PLC) 91. The PLC, with input from the chlorine analyzer 51, controls the automatic blow-off of water to maintain chlorine residual levels while collecting data. The chlorine analyzer has the capability to monitor either free or combined chlorine levels in the water distribution system. The device also allows the user to manually flush water from the line with the simple push of a button, allows a minimum of eight automatic sampling times, has a maximum flush length per sampling time, and allows the end user to program the desired and minimum chlorine levels.

A constant voltage regulator 95 is provided between the generator 73 and electronics, such as the PLC 91, to permit the batteries 75 to be charged at a higher voltage than the voltage required by the electronics.

All flushed water hits the wheel 71 of the turbine generator, which will charge the 210 Ampere-hour deep cycle batteries 75. The batteries 75 power substantially the entire device; the latching solenoids 39 and 61 are powered by 9-volt batteries. The device uses a voltage sensing relay 97 to maintain a certain level of power in the batteries 75 at all times. Should the voltage drop below a certain level the PLC will receive an alarm from the relay 97 and will cause the main valve 33 to begin flushing, thereby driving the turbine to charge the batteries. While charging, the batteries 75 are monitored via the redundant charge diversion controllers 79 that will automatically "burn off" any excess power using resistors to prevent the deep cycle batteries from being over-charged or damaged.

As described above, four separate temperature sensors (thermostats) 81 are located in different areas of the enclosure (the four upright corner posts) to account for any possible drafts allowed by the enclosure access panels and other localized cooling.

Should a thermostat 81 send a low temperature reading to the PLC 91, the PLC checks to see whether the latching valve 33 is open. If it is, the PLC 91 turns on the high efficiency fan heater 83 to heat the enclosure. The turbine must be running for the heater to be turned on. If the hydrant is not flushing at the time a low temperature is detected, the PLC receives an alarm and will start a flushing sequence.

Figure 9:
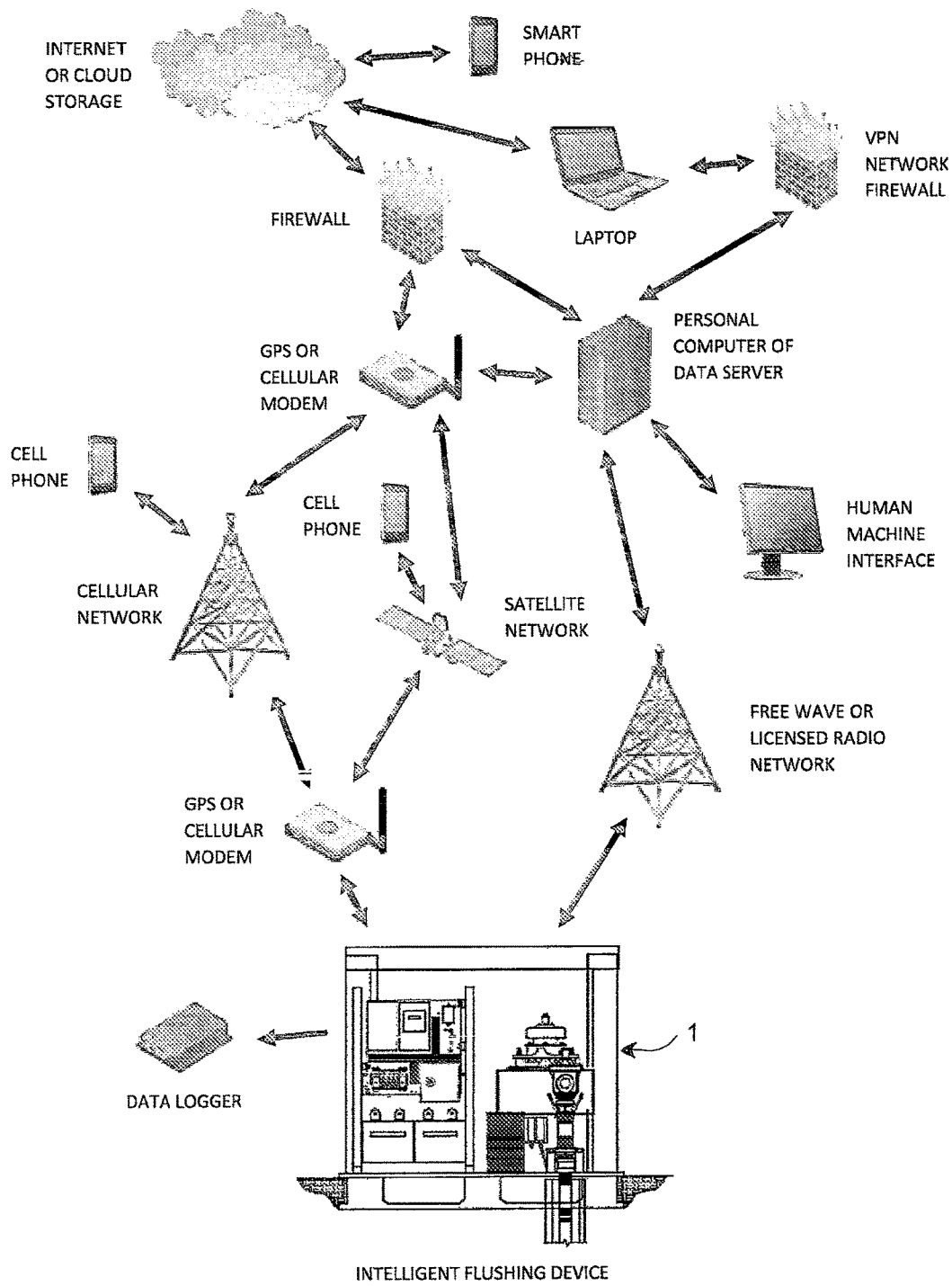
FIG. 9 is a networking diagram showing illustrative ways in which the device of FIGS. 1-8 can be networked for sending commands to the device and receiving information from the device.

As shown in FIG. 9, the device 1 is designed to allow the end user to interface with a SCADA system via remote communication.

The PLC may be programmed to open the chlorine sensor system sampling solenoid valve 59 on a timed basis, or based on prior readings, or by a remote operator. When the chlorine sensor 51 signals indicate to the PLC that chlorine levels have fallen below a predetermined threshold, the PLC opens the main valve 33 until chlorine levels reach a desired value or a maximum flush time has been reached.

If the PLC detects that voltage levels in the batteries 75 have fallen below a set level, it opens the main valve 33 to run the turbine until the batteries are fully charged, then continues for a set period to trickle charge the batteries while throwing most of the turbine's output to the dissipaters 55.

If the temperature sensors 10 are of a type which sends temperature information rather than a simple under-temperature reading, when the PLC detects that the temperature has fallen below a predetermined value, illustratively 37° F. (3° C.), it opens the main valve 33 to run the turbine 53 and connects the turbine to operate the fan heater 83. It will be noted that the turbine may simultaneously charge the batteries 75 and generate heat through the dissipaters 55. When the temperature sensors 10 detect that the temperature within the enclosure has reached a set point, illustratively 45°-47° F., (7-8° C.) the main valve 33 is closed. Because the valve 33 is controlled by a latching (bistable) solenoid 39, it should determine the state of the valve before issuing open or close commands.

Figure 6A:
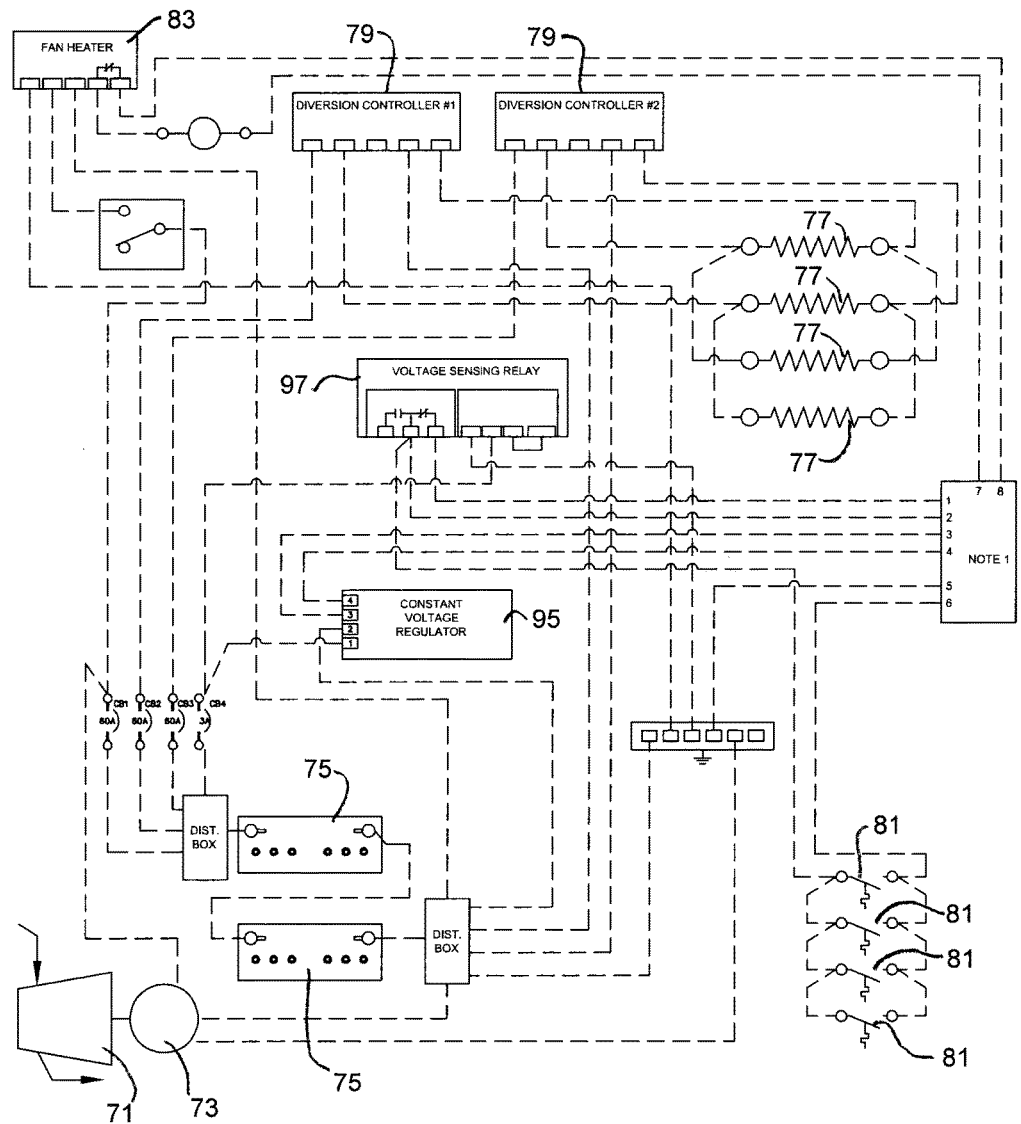
FIGS. 6A and 6B are an electrical schematic of the device.
Figure 6B:
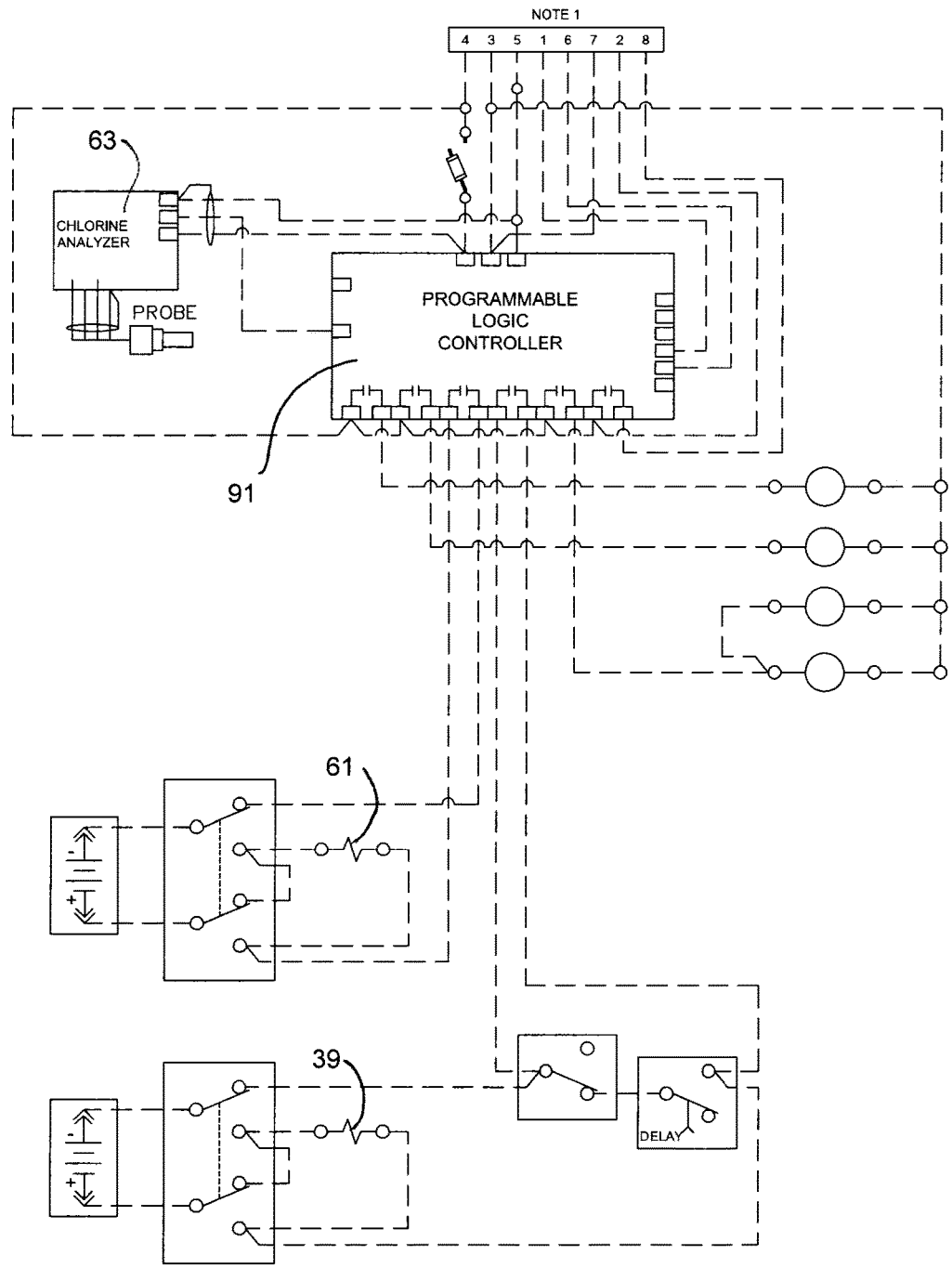
Figure 7:
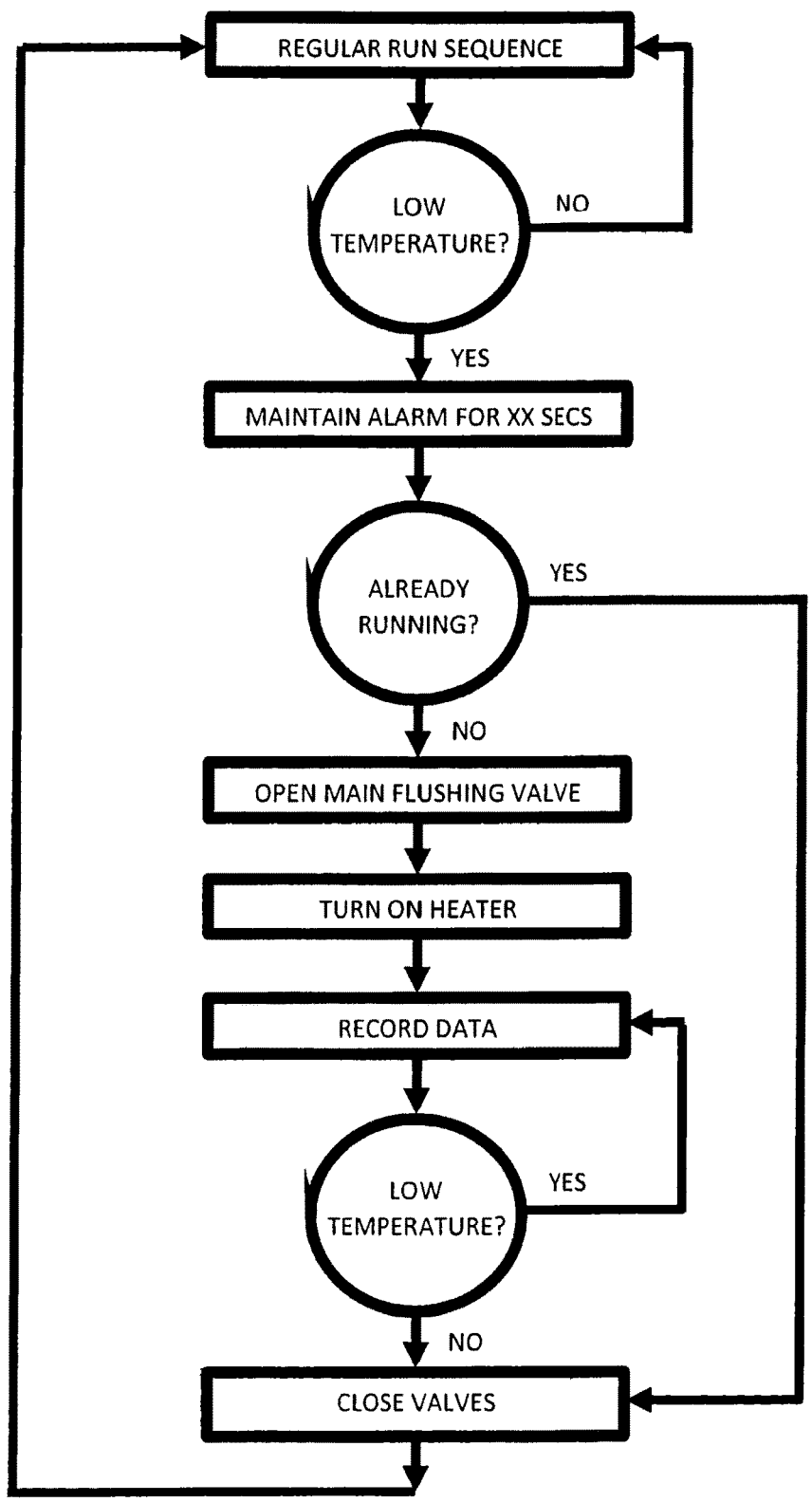
FIG. 7 is a logic diagram illustrating the operation of the device of FIGS. 1-6 to maintain its temperature.
Figure 8:
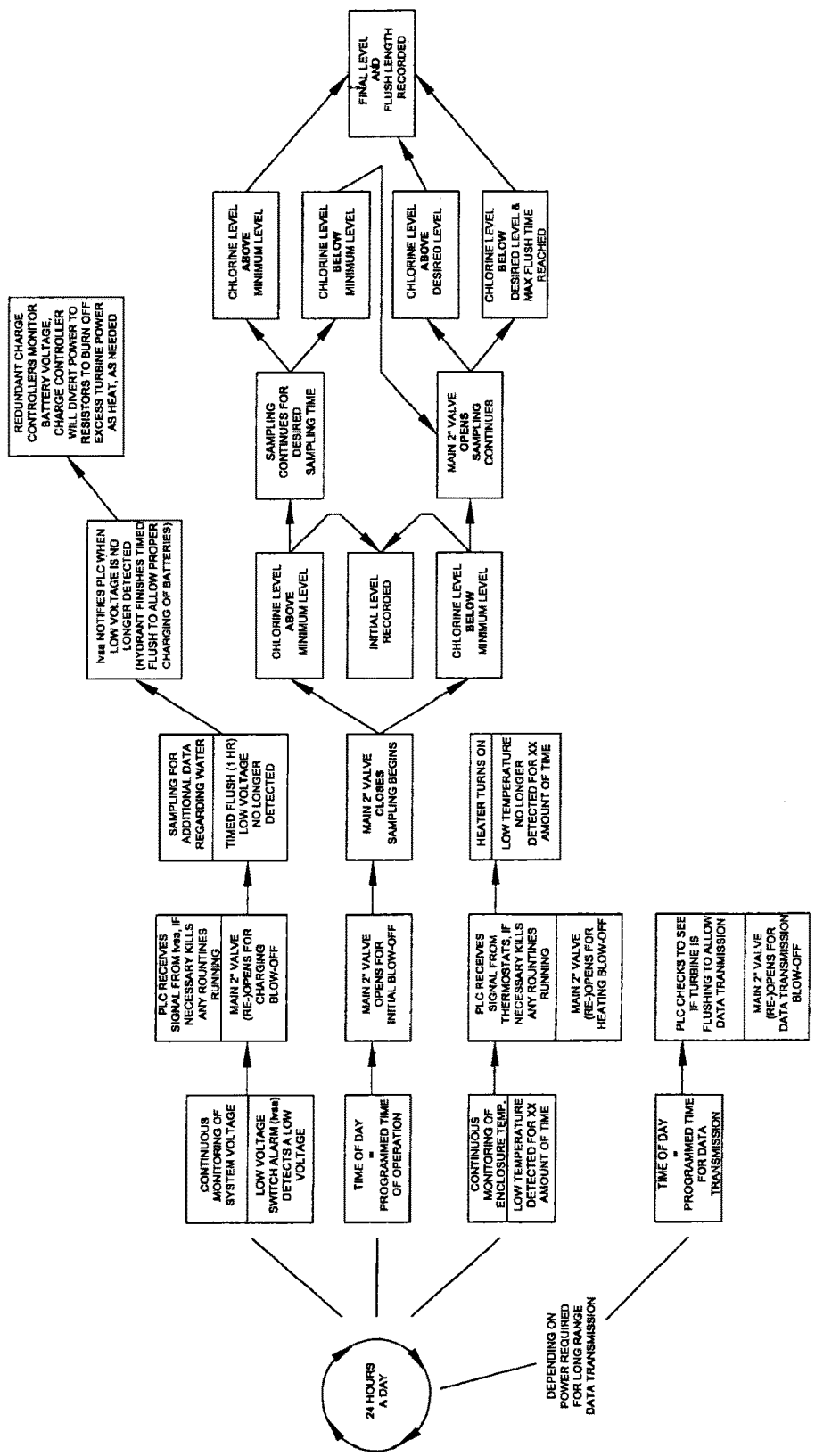
FIG. 8 is a logic diagram illustrating typical operation of the device of FIGS. 1-7.

Details of the operation of the device are set out in FIGS. 7 and 8, and the circuitry of the device is shown in FIGS. 6A and 6B.

Numerous variations in the device of the invention, within the scope of the appended claims, will occur to those skilled in the art and are a part of the present invention.

The invention claimed is:

1. A device attached to a subterranean water supply, the device comprising a valve operable to flush water from the subterranean supply through the device, a turbine operable to generate electricity when water is flushed through the device, an enclosure containing the valve, a temperature sensor operable to sense temperature within the enclosure, a heater operably connected to the turbine and being operable to heat the enclosure, and a control system operable to open the valve to cause the turbine to operate the heater when the temperature sensor indicates the approach of a dangerously low temperature.

2. The device of claim 1 wherein the device comprises a timer which periodically flushes water through the system.

3. The device of claim 1 wherein the device both flushes water and samples at least one condition of the water flowing through it.

4. The device of claim 1 wherein the enclosure is insulated to a thermal resistance of at least about R-9 (U.S.) (R-1.6 SI).

5. The device of claim 1 wherein the device comprises a condition sensor which senses at least one condition of the subterranean water and opens the valve to flush the water through the device in response to a condition sensed by the condition sensor.

6. The device of claim 5 wherein the condition sensor is configured to sense a condition of a sample of water drawn by the device from the subterranean water supply.

7. The device of claim 1 wherein the turbine is located downstream of an outlet of the flushing device.

8. The device of claim 7 further including a nozzle in the outlet, the nozzle guiding an exit stream into vanes of the turbine.

9. The device of claim 1 further comprising at least one rechargeable battery within the enclosure, and wherein an electrical resistive dissipater is electrically connected to the turbine generator to prevent overcharging the battery and to act as a heater.

10. The device of claim 9 further comprising a fan-heater energized by at least one of the turbine and the battery.

11. The device of claim 9 wherein the temperature modification device comprises at least one of a fan and a heater, the fan or heater being energized by at least one of the turbine and the battery.

12. A device attached to a subterranean water supply, the device comprising a valve operable to flush water from the subterranean supply through the device, a turbine operable to generate electricity when water is flushed through the device, an enclosure containing the valve, a temperature sensor operable to sense temperature within the enclosure, a temperature modification device operably connected to the turbine and being operable to heat or cool the enclosure, and a control system operable to open the valve to cause the turbine to operate the temperature modification device when the temperature sensor indicates the approach of a dangerously low or high temperature.

13. The device of claim 12 wherein the device comprises a condition sensor which senses at least one condition of the subterranean water and opens the valve to flush the water through the device in response to a condition sensed by the condition sensor.

14. The device of claim 12 further comprising at least one rechargeable battery within the enclosure, and wherein an electrical resistive dissipater is electrically connected to the turbine generator to prevent overcharging the battery.

15. A method of operating a device connected to a subterranean pressurized water supply and unconnected to an external source of electricity, the device comprising an insulated housing and an electronics package in the insulated housing, the method comprising sensing a temperature within the insulated housing and, when the temperature drops below a predetermined value, running water from the pressurized water supply through the device to generate electricity to heat the enclosure.

16. The method of claim 15 wherein running water through the device operates a turbine connected to an electrical generator.

17. A method of operating a flushing and monitoring device connected to a subterranean pressurized water supply and unconnected to an external source of electricity, the device comprising an insulated housing, a rechargeable battery in the housing, a turbine generator in the housing, and a water condition sensor in the housing, the method comprising sensing a temperature within the insulated housing, sensing a water condition, and sensing a battery charge level, and running water from the pressurized water supply through the device to run the turbine generator whenever any one of the temperature, water condition, or battery charge level reaches a value indicating the need for electrical energy.

18. The method of claim 17 wherein flow of flushing water through the device is controlled by a latching solenoid, and wherein an electronic control senses whether the latching solenoid is open or closed before trying to open or close the solenoid.

19. The method of claim 17 wherein the water condition sensed is a concentration of disinfectant in the water.

20. The method of claim 19 wherein the disinfectant is chlorine.

* * * * *